(12) United States Patent
Pfeiler

(10) Patent No.: US 7,539,285 B2
(45) Date of Patent: May 26, 2009

(54) DEVICE FOR EXPOSURE FIELD MONITORING IN A RADIATION THERAPY APPARATUS

(75) Inventor: Manfred Pfeiler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/105,353

(22) Filed: Apr. 18, 2008

(65) Prior Publication Data
US 2008/0260099 A1 Oct. 23, 2008

(30) Foreign Application Priority Data
Apr. 18, 2007 (DE) ...................... 10 2007 018 288

(51) Int. Cl.
*A61N 5/10* (2006.01)
(52) U.S. Cl. ........................................ 378/65; 378/119
(58) Field of Classification Search ................... 378/62, 378/64, 65, 119, 121, 147–153, 156–159, 378/205; 600/407, 427
See application file for complete search history.

(56) References Cited

U.S. PATENT DOCUMENTS

| | | | | |
|---|---|---|---|---|
| 5,396,889 A | 3/1995 | Ueda et al. | ................... | 600/407 |
| 5,471,516 A | 11/1995 | Nunan | ......................... | 378/65 |
| 6,134,295 A | 10/2000 | Kirby et al. | ................... | 378/65 |
| 6,445,766 B1 | 9/2002 | Whitham | ..................... | 378/65 |
| 2004/0076260 A1 | 4/2004 | Charles, Jr. et al. | ......... | 378/124 |

FOREIGN PATENT DOCUMENTS

| DE | 102 40 912 A1 | 3/2004 |
|---|---|---|
| EP | 0 060 771 A1 | 3/1982 |

*Primary Examiner*—Courtney Thomas
(74) *Attorney, Agent, or Firm*—Schiff Hardin LLP

(57) ABSTRACT

In a device for exposure field monitoring of a therapeutic radiation exposure field with diagnostic x-ray image quality with the same or nearly the same projection as in therapeutic radiation, the focal spot from which the diagnostic radiation emanates is designed to cause the diagnostic radiation to penetrate the patient in the same or nearly the same projection as the therapeutic radiation located at the target of the radiation therapy apparatus or in close proximity thereto.

3 Claims, 3 Drawing Sheets

DEVICE FOR EXPOSURE FIELD MONITORING IN A RADIATION THERAPY APPARATUS

BACKGROUND OF THE INVENTION

1. Field of the Invention

The present invention relates to therapeutic radiation apparatuses of the type wherein monitoring of the therapeutic radiation exposure field in the subject is undertaken by diagnostic imaging of the subject.

2. Description of the Prior Art

Like surgery and chemotherapy, radiation therapy is an essential means of tumor therapy. Normally high-energy x-ray radiation or gamma radiation is used that penetrates the body, so as to reach a deep-lying tumor and thereby deliver energy to the tissue of the tumor. With the exposure of the tumor to a radiation beam that is directed at the tumor from different directions in the course of the exposure time, it can be achieved that the tumor is always exposed during the duration of an exposure and the tissue in front of and behind the tumor (including the skin) are exposed only intermittently. In this manner a high radiation dose can be applied in the tumor with the therapeutic exposure apparatuses while the other irradiated tissue receives only a fraction (and as slight a fraction as possible) of the radiation dose as the tumor.

Newly emerged diagnostic methods (such as computed tomography), which also enable a more precise exposure planning have already served for more than thirty years in the development toward maximization of the radiation dose in the tumor tissue and minimization in the tumor-free tissue. With the requirement of increased exposure precision, the possibility has additionally developed to monitor the adherence to the exposure field set according to the plan by means of imaging during the exposure process.

After it has passed through the patient body, the therapeutic radiation beam proceeds to the image-acquiring system. In the simplest case this is a radiographic film system that is formed of a film and a radiation-converting luminophore foil that for its part exposes the film.

Systems of this type have been relied on for more than twenty years since the beginning of the imaging exposure field monitoring, known as portal imaging generation of or a verification image for the exposure field. The radiographic images generated with these systems and depicting the exposure field naturally have unsatisfactory properties with regard to contrast and sharpness in comparison to the images generated with a diagnostic x-ray system. This is due to the high energy of the therapeutic radiation (that, for example, lies in the range of a few MeV) and interaction of the focal spot of the radiation source (which focal spot is a few millimeters in size) with the radiation geometry provided by the exposure apparatus. The disadvantageous absorption or image conversion properties of the radiographic image system for this high-energy radiation to which it is exposed represent additional problems.

In spite of the insufficient image quality, such images are usable for the monitoring of the exposure field and the adjustment thereof with regard to the body of the patient, so that such systems have been developed and improved, for example by the use of luminophore-coated metal foils that offer a higher quanta yield and thereby improve the image quality. Use was made of the fact that, through the absorption of quanta in metal, electrons released from this metal contribute to the exposure of the film by light excitation in the luminophore.

FIG. 1 shows the basic design of a known exposure apparatus of the type described above. The patient 1 is borne on a table plate 3 that can be displaced at the foot 2 of a patient bed, and that is height-adjustable. The exposure apparatus includes the base 5 (firmly connected with the floor 4) that carries an extension arm 7 that can be rotated around the rotation axis 6, on which extension arm 7 the radiator 8 is mounted. The radiation beam 10 is shaped (in terms of its cross-section) by a collimator 9 and exits from the collimator 9, which is associated with the radiator 8. The patient 1 is positioned with the table plate 3 such that the radiation beam 10 penetrates a tumor located in the shoulder region in the depiction; the tumor lies in the rotation axis 6 of the exposure apparatus. The radiation beam 10 penetrating the patient exits the opposite side of the patient 1 as a radiation beam 10' after surrendering energy in the body. It then strikes the radiation detector 11 (having two edges 11' appearing in the side view) at the top side, at which it is absorbed. The environment of the exposure apparatus is thus protected from the radiation beam 10' exiting from the patient, which otherwise would freely radiate in space depending on the position of the extension arm 7.

However, the radiation detector 11 shown in FIG. 1 can serve not only for radiation capture but (according to FIG. 2) can also serve as a support (carrier) for an imaging system 12 that is shown with its upper edges 12' in an angled position of the extension arm 7. In the simplest case this system 12 is a radiographic film system is formed of a radiographic film in contact with a radiation-converting foil that exposes the film in addition to the radiation directly absorbed thereby. The radiation beam 10' striking the imaging system 12 is the radiation beam 10 that was modulated upon passage through the patient 1 corresponding to the radiation attenuation properties of the traversed body segment, and therefore records on the film of the imaging system 12 a radiogram of the respective body section acquired by the radiation beam 10.

The x-ray or gamma radiation emitted by the radiator 8 usually generated by a linear accelerator 13 shown in FIG. 3. In this accelerator 13, an electron beam 15 exits from an electron gun 14, the electrons, the electron beam 15 are accelerated to high energies (for example 6 MeV) in the axis 16 of the waveguide structure 17 fed with radio-frequency energy by its axial electrical field.

These electrons of high energy exit from the waveguide structure 17 through the vacuum window 18 at the end of said waveguide structure 17 and strike the target 19 (which is a thin disc made from suitable heavy metal). In this target 19 the electron beam 15 generates high-energy x-rays or gamma rays that exit from the focal spot 20 on the side of the target 19 facing away from the electron beam 15 and form a radiation beam 21. The recumbent board 21 is brought into the position needed for the exposure by the primary collimator 22 and the secondary collimator 23, the latter corresponding to the collimator 9 shown in FIG. 1 and FIG. 2. The radiation beam 21 thus becomes the radiation beam 10 that enters into the patient 1 according to FIG. 1 and FIG. 2. FIG. 3 shows a compensation filter 24 between the primary collimator 22 and the secondary collimator 23. This compensation filter 24, due to its shape in the core of the radiation beam 21, reduces the excessive radiation power there (due to the given type of radiation generation) and therefore normalizes this power across the cross-section of the radiation beam 21. The secondary collimator 23 (shown in FIGS. 1 and 2 as collimator 9) has the task of removing the diffuse edge zones of the cross-section of the radiation beam 21 that are left by the primary collimator 22 due to the beam geometry before the radiation beam 21 leaves the radiator 8 as radiation beam 10.

FIG. 3 shows only the basic components of the radiator 8. Dose measurement chambers (such as, for example, structural elements for deflection of the accelerated electron beam 15) that enable advantageous designs of the radiator 8 are not shown.

Since the development of the system described above, therapeutic radiation exposure apparatuses have experienced further improvements, for example with regard to collimators for more sharply defining the edges of the exposure field and also with regard to the possibility to continuously alter the radiation power in the exposure field dependent on the radiation direction by adaptation to the changing projections of the tumor and the tissue to be spared, if at all possible, by the radiation.

The means for imaging diagnostics have likewise increasingly had a higher precision for diagnostics and therefore also localization of sources to be irradiated in accord with a steadily improving therapy planning.

The requirements for manageability, precision and reliability of the exposure field monitoring or just the portal imaging, therefore have increased, with the image quality being accorded a significant role. Manageability has played a role because, to assess the film in the imaging system according to FIG. 2, this had to be developed first and in a time-consuming manner. A first step for improvement of the exposure field monitoring for the imaging system 12 according to FIG. 2 was to replace the radiographic film system with a radioscopy system that passes the light density (luminance) generated thereby due to the radiation to a system that is formed by an optical image intensifier and a downstream television system. The relaying of the light density image to the image intensifier via a mirror allowed radiation-sensitive parts of the electronics of the image intensifier-television system to be arranged outside of the therapeutic radiation beam.

However, the decisive improvement of the image quality of the portal imaging occurred by the use of regular diagnostic x-ray radioscopy devices to irradiate the body sections involved in the therapeutic radiation. For instance, in the first half of the 1990's, exposure devices were known in which the radiator of the diagnostic x-ray system was firmly connected with the radiator 8 (shown in FIGS. 1 and 2) of the exposure apparatus, such that the central rays of the therapeutic radiation beam 10 as well as the diagnostic rays strike in what is known as the isocenter (defined by the rotation axis 6 of the exposure apparatus) and move in small rotary movements, and enclose an optimally small angle, such as angles of 37° and 45°, for example. Naturally identical projections for the therapeutic and diagnostic radiation beams can be realized in principle here because of the identical beam geometries. Such identical projections, occur only in succession (thus not be simultaneous) with regard to the radiated body sections. For an exposure field monitoring either the depth diaphragm of the diagnostic system must emulate the collimator for the therapeutic radiation, or an emulation of the therapeutic exposure field must be superimposed on the image acquired with the diagnostic radiation beam under consideration of the respective different positions of the two central rays. An advantage of such an arrangement is that it offers the possibility for the diagnostic system to be equipped with a conventional x-ray intensifier that, like the connected image electronics, remains outside of the therapeutic radiation beam.

A radiation therapy apparatus is described as a concept in "Imaging Systems for Medical Diagnostics", edited by A. Oppelt; Editor: (Siemens Aktiengesellschaft; Publisher: Publicis Corporate Publishing, Erlangen 2005, chapter 17.1 "Imaging for radiation therapy") that represents an extension of FIG. 1 herein. This known radioscopy system is shown in FIG. 4 and has an x-ray radiator 25 for diagnostic radiation with an associated depth diaphragm or collimator 26 and an image-converting detector 28. The x-ray radiator 25 is mounted at the exposure apparatus by a crossbar 27 such that central ray of the emitted diagnostic radiation beam 29 is congruent with the central ray of the therapeutic radiation beam 10 according to FIGS. 1 and 2, but is directed in the opposite direction and therefore along the axis 16. The radiation beam 29' is the continuation of the radiation beam 29 after passage through the patient 1.

The detector 28 of the type known as a flat panel detector in which a luminophore layer converts the x-ray radiation into a light (luminescent) image that is in turn transduced by an array composed of amorphous silicon into electrical signals. An advantage of such a flat panel detector is that it can be irradiated without damage by the therapeutic radiation when only the associated electronics remain outside of this radiation.

The radioscopy system of the radiation therapy apparatus in FIG. 4 can therefore simultaneously irradiate the same body section as the therapy beam, but as shown in FIG. 4 this occurs in the opposite direction. Although the acquired body sections are therefore nearly identical, they can be non-identical due to the central projections in opposite directions. As used herein, simultaneously (or, more precisely, quasi-simultaneously) means that the radioscopy system is pulsed so that its radiation pulses are emitted in the time gaps of the pulsed therapeutic radiation.

The result is that, given the use of the described diagnostic x-ray systems for exposure field monitoring, the image quality accommodates the precision requirements for radiation therapy, but with the sacrifice of dispensing with the possibility to simultaneously acquire identical projections for the therapeutic and the diagnostic radiation beam in a given position of the exposure apparatus, which was provided in the first place in portal imaging from its inception. A particular advantage was that the image produced for the exposure field monitoring likewise identically showed the exposure field from the outset because the image according to FIG. 2 was produced with the radiation beam 10' exiting from the patient 1.

If portal imaging in its original form is therefore excluded from discussion due to insufficient image quality, the question remains as to which system should preferably be used: a system that offers a practically simultaneous verification image for the exposure field, but with a different distortion in comparison to an image of the original portal imaging (because, according to FIG. 4, the therapeutic radiation and diagnostic radiation pass through the body section irradiated by them in opposite directions), or a system with an image with a projection identical to the exposure field, but that shows the current exposure field with a time offset. In both cases the diagnostic radiation beam for the imaging has its own collimator or gating device that is thus not identical with the collimator device for the therapeutic radiation.

SUMMARY OF THE INVENTION

An object of the present invention is to provide a device for exposure field monitoring for a radiological therapy apparatus that offers diagnostic x-ray image quality with identical or nearly identical projections of the diagnostic and therapeutic radiation, and that also shows the effect of the collimator device for the therapeutic radiation beam, and that provides the possibility to monitor the exposure process simultaneously or nearly simultaneously.

This object is achieved in accordance with a first embodiment of the invention by a therapeutic exposure apparatus having a therapeutic radiation source that has an electron beam source that emits an electron beam and a target that is struck by the electron beam at a focal spot, causing high-energy therapeutic radiation to be emitted from said focal spot, and a diagnostic x-ray radiation source configured to also interact with the target at said focal spot to emit diagnostic x-ray radiation from the focal spot, causing said diagnostic x-ray radiation to irradiate a same body region of a subject as said therapeutic radiation with a same projection geometry as the therapeutic radiation. A radiation detector is irradiated by said diagnostic x-ray radiation to generate an image of the body section to monitor exposure of the body section by the therapeutic radiation.

The above object also is achieved in accordance with a second embodiment by a therapeutic exposure apparatus having a therapeutic radiation source that has an electron beam source that emits an electron beam, a target struck by the electron beam at a first focal spot, the electron beam causing high-energy therapeutic radiation to be emitted from the first focal spot as a therapeutic radiation beam having a radiation power, and a compensation filter located in a path of the radiation beam, that interacts with the therapeutic radiation to normalize the radiation power in said radiation beam.

A diagnostic x-ray radiation source interacts with the compensation filter at a second focal spot on said compensation filter to cause diagnostic x-ray radiation to be emitted from the second focal spot.

The compensation filter is located relative to the target to cause the first and second focal spots to be so close to each other that the diagnostic x-ray radiation irradiates a body section of a subject that substantially coincides with a body section of the subject irradiated by said therapeutic radiation, with heat respectively arising at the first and second focal spots being divided between the target and the compensation filter.

A radiation detector is irradiated by said diagnostic x-ray radiation to generate an image of the body section to monitor exposure of the body section by the therapeutic radiation.

The above object also is achieved in a third embodiment of the invention by a therapeutic exposure apparatus having a therapeutic radiation source that has an electron source that emits an electron beam, a target struck by the electron beam, the electron beam causing high-energy therapeutic radiation to be emitted from the target as a therapeutic radiation beam propagating along a therapeutic beam axis and having a radiation power associated therewith, and at least one therapeutic beam collimator that interacts with the therapeutic radiation to normalize the radiation power of said therapeutic radiation beam.

A diagnostic x-ray source emits a diagnostic x-ray beam, the diagnostic x-ray source being configured to emit the diagnostic x-ray beam along the therapeutic beam axis, and having an x-ray diaphragm system, separate from the at least one therapeutic beam collimator, that interacts with the x-ray diagnostic radiation to produce an x-ray diagnostic radiation beam that is configured to irradiate a body region of a patient in a diagnostic exposure field that is larger than a body region of the patient irradiated by the therapeutic radiation beam in a therapeutic exposure field.

A radiation detector detects the diagnostic x-ray radiation in the diagnostic exposure field after passing through the patient, to produce an image of the patient corresponding in size to the diagnostic exposure field that encompasses the region of the patient irradiated in the therapeutic radiation field.

An electronic image processor processes the image from said radiation detector produced by the x-ray diagnostic radiation to allow display of the image produced by said x-ray diagnostic radiation independently of an orientation of the therapeutic radiation field.

DESCRIPTION OF THE PREFERRED EMBODIMENTS

Figure 1:
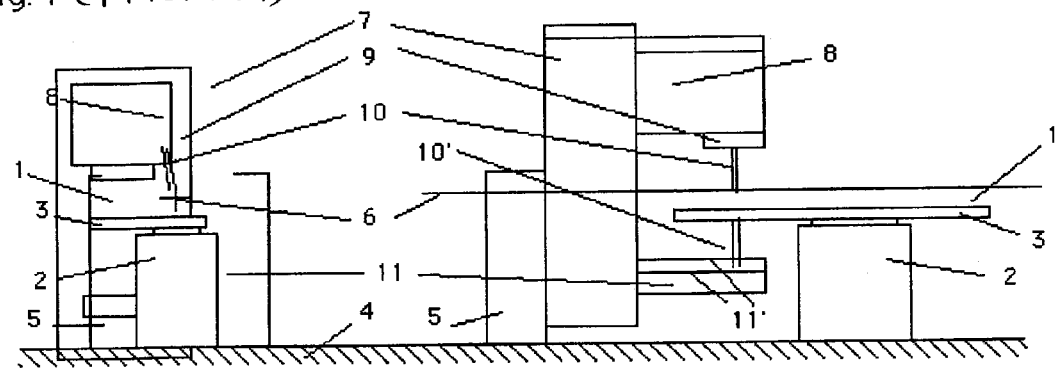
FIG. 1 illustrates a first version of a radiation therapy apparatus of the type known in the prior art.
Figure 2:
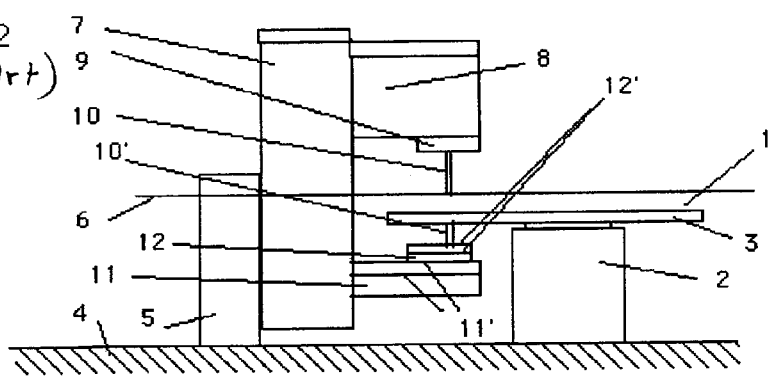
FIG. 2 illustrates a second version of a radiation therapy apparatus of the type known in the prior art.

Acquisition of the therapeutic and diagnostic radiation with identical projections simultaneously or virtually simultaneously (i.e. in immediate temporal alternation) is achieved by the focal spot 19 of the therapeutic radiation and the focal spot of the diagnostic radiation being located at the same point. According to FIG. 5, the radiation beam 20 of the diagnostic radiation exits from the radiator 8 just like the radiation beam 10 of the therapeutic radiation according to FIGS. 1 and 2 (not shown in FIG. 5). Both radiation beams 30 and 10 pass through the patient 1 in the same direction and exit from the patient 1 as a radiation beam 30' or 10'. The radiation power distribution provided with the radiation beam 30' across its cross-section is converted by the detector 28 (which is supported by the crossbar 27 in FIG. 5) and its downstream image electronics into an x-ray image of diagnostic quality.

Figure 6A:
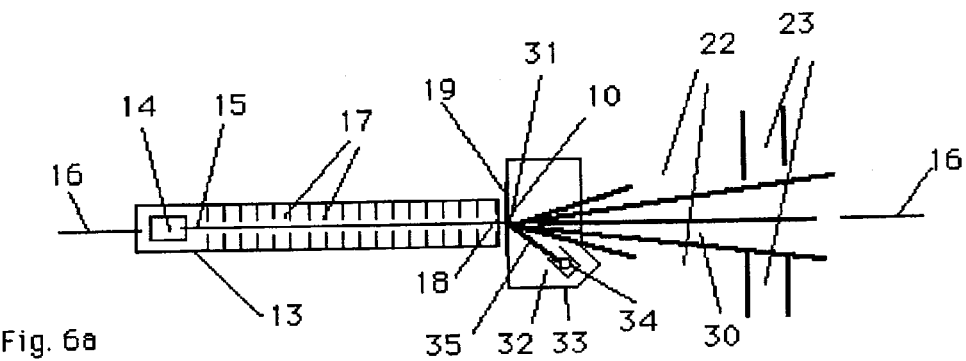
FIGS. 6a and 6b illustrate the operation of the therapy apparatus of FIG. 5.

According to FIG. 6a, this goal (to bring the focal spot 31 of the diagnostic radiation at the point of the focal spot 20 of the therapeutic radiation) is achieved by the target 19 following the electron beam accelerator 13 in the radiator 8 also serves as an anode of the diagnostic x-ray radiator 32, which furthermore includes the vacuum casing 33 and the cathode 34, from which an electron beam 35 is incident on the target 19 at the point of the focal spot 20. The target 19 is part of the vacuum casing 33. If the linear accelerator 13 is deactivated, the electron beam 15, and therefore the focal spot 20, thus are not present, but the focal spot 31 of the diagnostic radiation, characterized by the radiation beam 30, still exists so the system operates in imaging mode according to FIG. 6a.

Figure 6B:
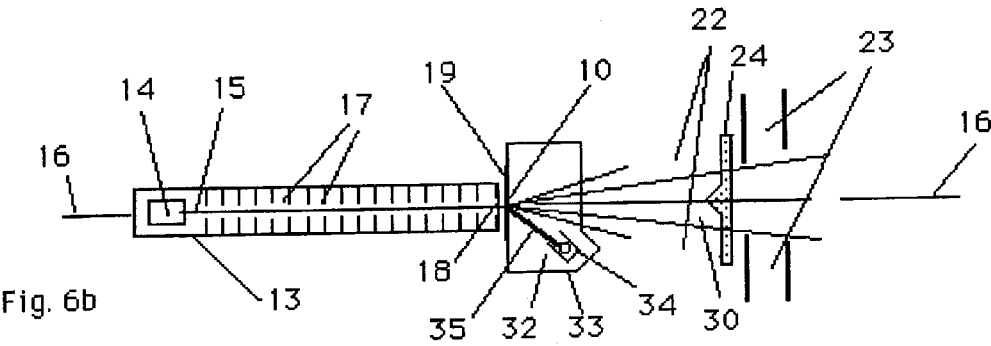

In the transition to the mode of the therapeutic exposure according to FIG. 6b, the diagnostic x-ray radiation 32 is deactivated, so the its electron beam 35 and the otherwise-generated focal spot 31 (at whose point the focal spot 20 of the therapeutic radiation strikes, characterized by the radiation beam 10) are absent as well. The compensation filter 24 described with regard to FIG. 3 is brought into the radiation beam 10 in the transition from imaging mode into exposure mode.

An arrangement according to FIGS. 6a and 6b with switching between the imaging mode and the exposure mode is not used to initially acquire an image for monitoring of the exposure field simultaneously with the exposure. The exposure field monitoring advantageously ensues before the exposure, wherein the anatomy in the environment of the planned radiation field can be graphically depicted in addition to the actual exposure field monitoring with identical settings of the diaphragms or, respectively, collimators 22 and 23 by enlargement of the diaphragm apertures. This occurs via a collimator exchange in the case of the collimator 22. Depending on the strategy of the exposure process and the design of the image processing system, both processes proceeding in alternation can be combined, for example, by the exposure field being masked or marked in the x-ray image of the environment.

An exposure field monitoring of diagnostic image quality occurring simultaneously or virtually simultaneously with the exposure can be enabled by the task of the compensation filter 24, namely the normalization of the therapeutic radiation beam 10 emitted by the focal spot 20, being taken over by the target 19, which for this purpose is equipped with a reinforced target thickness in its center.

Figure 3:
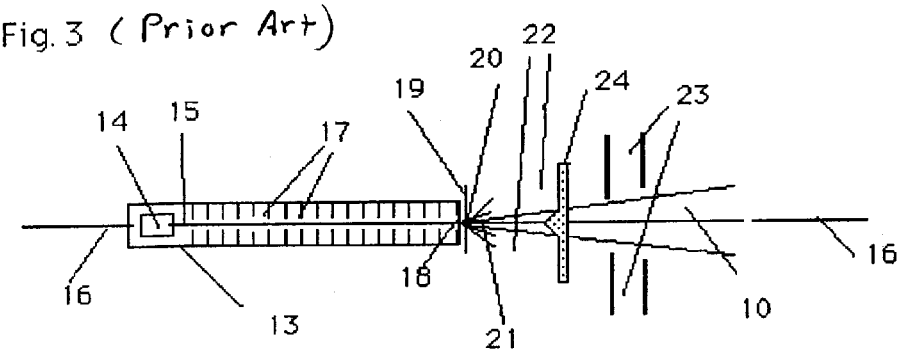
FIG. 3 schematically illustrates a known linear accelerator of the type used in the radiation therapy apparatuses of FIGS. 1 and 2.

Moreover, an arrangement according to FIGS. 6a and 6b also allows a different method for radiation therapy like that shown in FIG. 3, namely exposure with fast electrons. If the target 19 transducing the electron beam 15 into x-rays or gamma radiation is removed, like the compensation filter 24, the electron beam exiting from the vacuum window is thus available for an exposure with electrons. Instead of the target 19, in the arrangement in FIGS. 6a and 6b the diagnostic x-ray radiator would be to be removed from the beam path.

In an arrangement according to FIGS. 6a and 6b in which (as just described) the exposure field monitoring should ensue simultaneously with the exposure, the problem of the insufficient thermal load capacity of the target 19 (at which the electron beam 15 from the linear accelerator 13 as well as the electron beam 35 from the cathode 34 of the x-ray radiator 32 strike) could still exist.

Figure 7A:
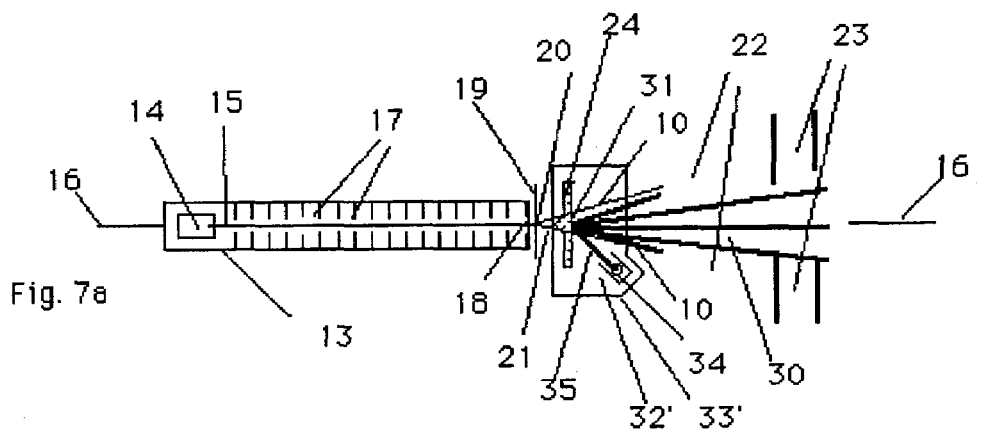
FIGS. 7a and 7b schematically illustrate the operation of a second embodiment of a therapy apparatus in accordance with the present invention.
Figure 7B:
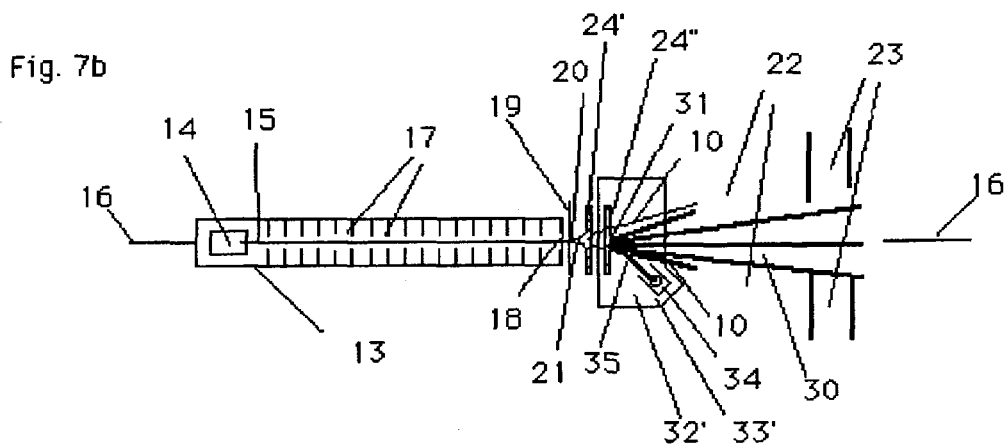

This problem is addressed in the arrangement according to FIGS. 7a and 7b. The arrangement in FIG. 7a is the same as in FIG. 3 up to the target 19. Here what is known as an independent x-ray radiator 32' with a vacuum casing 33' in which the target 19 is no longer integrated is available to generate the diagnostic radiation. The diagnostic x-ray radiator 32' now simultaneously uses the compensation filter 24 (which for this can be composed of a suitable composite material) acting on the therapeutic radiation as an anode, which the catheter 34 deflecting the electron beam 35 generated thereby onto the flat side of the compensation filter 24, such that the central ray of the radiation beam 30 emanating from its focal spot 31 coincides with the central ray of the therapeutic radiation beam 21 (of which only two edge rays are shown in FIG. 7) emanating from the focal spot 20. In FIG. 7a it can be seen that, although the focal spots 20 and 31 both lie on the axis 16, they do not coincide but rather have a finite separation from one another. It can be assumed that these can lie so close to one another that the differences in the distortion of the irradiated body parts of the patient 1 upon application of the radiation therapy application are negligibly small due to the given radiation geometries for the diagnostic as well as therapeutic radiation.

In the transition from FIG. 7a to FIG. 7b the compensation filter 24 is, so to speak, divided into the plate 24" and a "remainder compensation filter" 24', and the plate 24" is used as an anode of the diagnostic x-ray radiator 32'. The plate 24" should attenuate the therapeutic radiation as little as possible, but in any case uniformly over the cross-section of its radiation beam 21; the remainder compensation filter 24' should provide for the normalization of the radiation power across the cross-section of the therapeutic radiation beam 21 exiting from the focal spot 20. The remainder compensation filter 24' can be inserted into the radiation beam 21 of the therapeutic radiation inside or outside of the vacuum casing 33' of the x-ray radiation 32'. The anode of the x-ray radiator 32 in the form of the plate 24" would additionally allow this plate 24" to also be executed as a rotary anode, depending on the thermal load.

Figure 8:
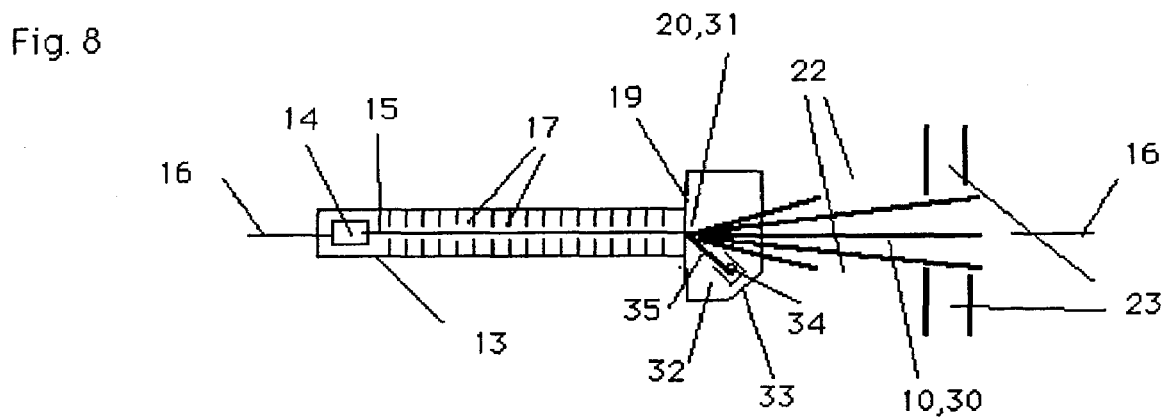
FIG. 8 schematically illustrates a further embodiment of a therapy apparatus in accordance with the present invention.

FIG. 8 is based on the ideas presented with regard to FIGS. 6a and 6b, with the task of the compensation filter 24 (namely the normalization of the therapeutic radiation beam 10 emitted by the focal spot 20) being taken over by the target 19. FIG. 8 explains the concept of a simplified radiator 8 in which a vacuum window 18 for the electron exit according to FIGS. 3 and 6a and 6b is omitted and the target 19 takes its place. This simplification removes the usage of the linear accelerator 13 for radiation therapy with electron radiation.

The arrangements presented in FIGS. 7a and 7b and 8 do in fact allow an exposure field monitoring with diagnostic x-ray radiation but not a representation of the anatomical surroundings. As stated above, the arrangement in FIGS. 6a and 6b allows this only when the target 19 takes over the task of the compensation filter 24 to achieve a uniform radiation power curve across the cross-section of the therapeutic radiation beam 10.

It may be useful in the method of radiation therapy to forego identical projections for the therapeutic radiation beam 10 and the diagnostic radiation beam 30 when the projections are only directed in the same direction, thus the radiations proceed in the same direction and the central rays of both beams 10 and 30 lie on an axis in order to therefore achieve the advantage of a representation of the environment with diagnostic x-ray radiation during the exposure process. For this purpose, the diagnostic x-ray radiator would have to lie after the collimators 22 and 23 as viewed in the direction of the patient 1, and would be permeable for the therapeutic radiation beam 10 (comparable with the situation in FIG. 7b) and would have to have its own gating device.

Figure 4:
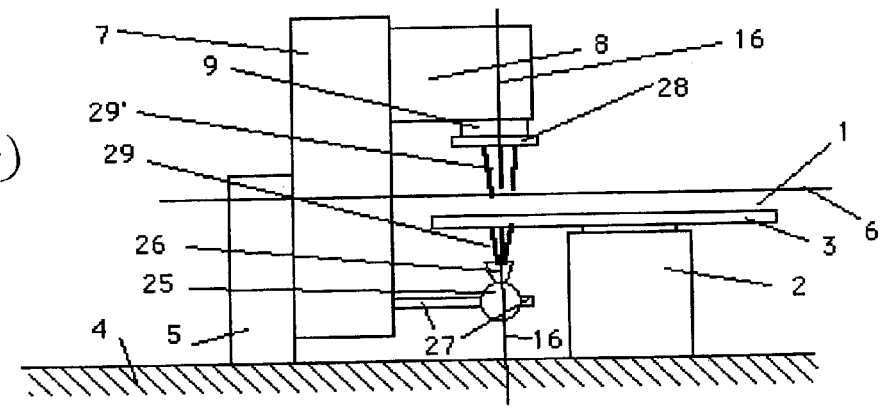
FIG. 4 illustrates a therapy apparatus with portal imaging of the type known in the prior art.
Figure 5:
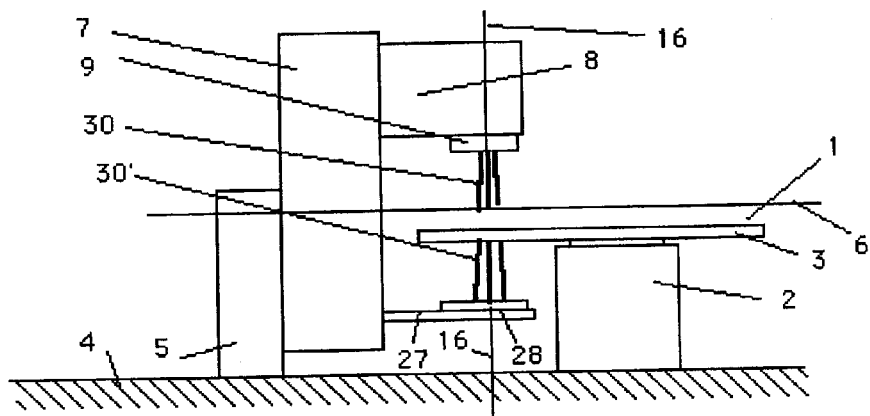
FIG. 5 schematically illustrates a therapy apparatus constructed and operating in accordance with the present invention, in a first embodiment.
Figure 9:
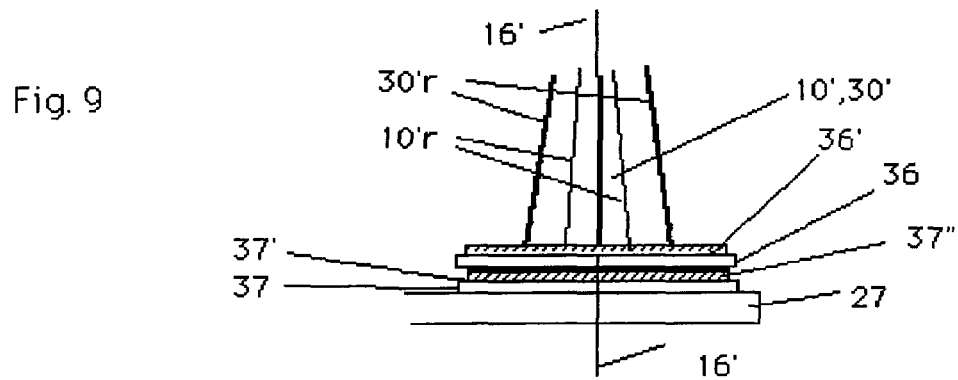
FIG. 9 illustrates a detector device for use in accordance with the present invention.

According to FIG. 9, the therapeutic radiation beam 10' exiting from the patient 1 and the diagnostic radiation beam 30' exiting from the patient 1 then strikes a detector arrangement simultaneously or virtually simultaneously (thus intermittently in rapid sequence and "at time gaps"), the detector arrangement being mounted on the crossbar 27 as in FIG. 5. This detector arrangement has two flat panel detectors lying one atop the other in which (as in the flat panel detector 28 described with regard to FIG. 4) x-rays or gamma radiation striking a luminophore layer are converted into a light image that is in turn transduced into electrical image signals by an array formed of amorphous silicon.

In FIG. 9 this detector device has an overlying flat panel detector with the array 36 and luminophore layer 36' that is designed for imaging with diagnostic x-ray radiation and the underlying flat panel detector with the array 37 and luminophore layer 37', wherein the luminophore layer 37' is applied on a metal foil 37". As already noted, the metal foil 37" serves for the sufficient absorption of quanta of the high-energy therapeutic radiation, which releases electrons in the metal of the foil that cause the luminophore layer to luminescence additionally or at all.

In terms of the image, the upper flat panel detector thus effectively absorbs with its luminophore layer 36' the diagnostic x-ray radiation striking it, characterized in FIG. 9 by the radiation beam 30' with the two drawn edge rays 30' r.

If it is furthermore assumed that the arrays 36 and 37 made from amorphous silicon can essentially pass the high-energy therapeutic x-ray radiation unattenuated, the high-energy therapeutic radiation of the exposure field (characterized by the radiation beam 10' with the two drawn edge rays 10' r) thus reaches the lower flat panel detector that transduces it into electrical image signals.

If the image data generated with the diagnostic x-ray radiation arrive virtually simultaneously (thus intermittently in rapid succession and "at time gaps") with the image data that the high-energy therapeutic radiation generates, a diagnostic x-ray image of the surroundings of the exposure field and an image of the exposure field is acquired practically simultaneously.

It is noted that, due to the geometry of the radiation beams 10 and 10', and 30 and 30', generating them, the images differ merely in the different magnifications with which different planes of the irradiated body section of the patient 1 are presented because the central rays of the radiation beam lie on the common axis 16' and the addressed planes in the irradiated body section of the patient 1 lie perpendicular to this.

For example, the magnifications of the plane in which a source to be exposed lies can be matched for both image types via a suitable image processing (which then also approximately applies for planes adjacent to this selected plane), such that a comparison of the images of both image types is made easier.

For the described, virtually simultaneous generation of the image data (only the radiation of diagnostic energy or the radiation of therapeutic energy then occurs at one point in time in the arrangement according to FIG. 9), it means that from the outside it is not a problem to also operate each of the two flat panel detectors in the reverse of the sequence of array and luminophore layer; the respective radiation would only penetrate the array of the considered detector in order to then be converted into light in the associated luminophore layer, wherein the metal film 37" would again have to lie on the outside of the luminophore layer 37' (thus on the side facing turned away from the array 37) in the flat panel detector for therapeutic radiation. Such considerations would enter into an optimization of the image system, for example with regard to activating a flat panel detector for diagnostic radiation for therapeutic radiation when the latter would actually be effective for diagnostic radiation via light generation in the luminophore layer 36' during its existence in the flat panel detector, and the light generated by it would not decay fast enough up to the usage of the diagnostic radiation.

In principle the detector arrangement according to FIG. 9 should also be able to be operated in "real simultaneity" for the generation of images of both types (meaning that diagnostic and therapeutic radiation occur at the same times) when the upper flat panel detector with the array 36 and the luminophore layer 36' allows the therapeutic radiation to pass, and possible remaining radiation of diagnostic energy that is allowed to pass is impeded by the metal foil 37", and thus is not active.

Two focal spots that are symmetrical to the position of the focal spot 31 can be used for stereoscopic x-ray imaging, which can be useful in and of itself as well as to alleviate thermal unloading of the target 19 charged by focal spots 20 and 31 of the therapeutic and diagnostic radiation, as in FIG. 8, for example.

With regard to the system of the double detector according to FIG. 9 should be noted that one system reading out the arrays and leading to the image could suffice for image transfer and evaluation given an operation (already mentioned repeatedly) in the sense of the virtually simultaneous occurrence of therapeutic and diagnostic radiation (thus intermittently and "in time gaps" in rapid sequence) for the arrays 36 and 37. Similar electrical connections of the two arrays 36 and 37 would be interconnected. Since the light images generated by the associated luminophore layers 36' and 37' would be transferred in the rhythm of the radiation pulses of the therapeutic and diagnostic radiation on the associated arrays, the image transfer system would just additionally have to take on the task of sorting the image signals incident in the rhythm of the radiation pulses, namely into image signals only for the image with diagnostic radiation and image signals only for the image with therapeutic radiation.

Following this concept of a common image electronics for both flat panel detectors according to FIG. 9 also leads to an arrangement in which both luminophore layers 37' and 37' act on a common array, assuming that this can be activated approximately comparably from both sides via the light images generated by the luminophore layers.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapeutic exposure apparatus comprising:
a therapeutic radiation source comprising an electron beam source that emits an electron beam and a target, struck by said electron beam at a focal spot, causing high-energy therapeutic radiation to be emitted from said focal spot;
a diagnostic x-ray radiation source configured to also interact with said target at said focal spot to emit diagnostic x-ray radiation from said focal spot, causing said diagnostic x-ray radiation to irradiate a same body region of a subject as said therapeutic radiation with a same projection geometry as said therapeutic radiation; and
a radiation detector that is irradiated by said diagnostic x-ray radiation to generate an image of said body section to monitor exposure of said body section by said therapeutic radiation.

2. A therapeutic exposure apparatus comprising:
a therapeutic radiation source comprising an electron beam source that emits an electron beam, a target struck by said electron beam at a first focal spot, said electron beam causing high-energy therapeutic radiation to be emitted from said first focal spot as a therapeutic radiation beam having a radiation power, and a compensation filter located in a path of said radiation beam, that interacts with said therapeutic radiation to normalize the radiation power in said radiation beam;
a diagnostic x-ray radiation source that interacts with said compensation filter at a second focal spot on said compensation filter to cause diagnostic x-ray radiation to be emitted from said second focal spot;
said compensation filter being located relative to said target to cause said first and second focal spots to be so close to each other that said diagnostic x-ray radiation irradiates a body section of a subject that substantially coincides with a body section of the subject irradiated by said therapeutic radiation, with heat respectively arising at said first and second focal spots being divided between said target and said compensation filter; and
a radiation detector that is irradiated by said diagnostic x-ray radiation to generate an image of said body section to monitor exposure of said body section by said therapeutic radiation.

3. A therapeutic exposure apparatus comprising:

a therapeutic radiation source comprising an electron source that emits an electron beam, a target struck by said electron beam, said electron beam causing high-energy therapeutic radiation to be emitted from said target as a therapeutic radiation beam propagating along a therapeutic beam axis and having a radiation power associated therewith, and at least one therapeutic beam collimator that interacts with said therapeutic radiation to normalize said radiation power of said therapeutic radiation beam;

a diagnostic x-ray source that emits a diagnostic x-ray beam, said diagnostic x-ray source being configured to emit said diagnostic x-ray beam along said therapeutic beam axis, and comprising an x-ray diaphragm system, separate from said at least one therapeutic beam collimator, that interacts with said x-ray diagnostic radiation to produce an x-ray diagnostic radiation beam that is configured to irradiate a body region of a patient in a diagnostic exposure field that is larger than a body region of the patient irradiated by the therapeutic radiation beam in a therapeutic exposure field;

a radiation detector that detects said diagnostic x-ray radiation in said diagnostic exposure field after passing through the patient, to produce an image of the patient corresponding in size to said diagnostic exposure field that encompasses the region of the patient irradiated in said therapeutic radiation field; and an electronic image processor that processes said image from said radiation detector produced by said x-ray diagnostic radiation to allow display of said image produced by said x-ray diagnostic radiation independently of an orientation of said therapeutic radiation field.

* * * * *